(12) United States Patent
MacMackin

(10) Patent No.: US 7,866,437 B2
(45) Date of Patent: Jan. 11, 2011

(54) STETHOSCOPE WITH ONE-HANDED OPERATION

(75) Inventor: Thomas G. MacMackin, Lafayette, NY (US)

(73) Assignee: TGMDVM, Inc., Lafayette, NY (US)

( * ) Notice: Subject to any disclaimer, the term of this patent is extended or adjusted under 35 U.S.C. 154(b) by 0 days.

(21) Appl. No.: 12/242,010

(22) Filed: Sep. 30, 2008

(65) Prior Publication Data

US 2010/0078257 A1    Apr. 1, 2010

(51) Int. Cl.
*A61B 7/02*     (2006.01)
(52) U.S. Cl. .................... 181/131; 181/137; 381/67; D24/134
(58) Field of Classification Search ............. 181/0.5, 181/18, 20, 21, 22, 131, 137; 381/67; D24/134
See application file for complete search history.

(56) References Cited

U.S. PATENT DOCUMENTS

| | | | | |
|---|---|---|---|---|
| 555,522 | A * | 3/1896 | Mitchell | 181/131 |
| 563,421 | A * | 7/1896 | Sheppard | 181/131 |
| 735,670 | A * | 8/1903 | Jones | 181/126 |
| 965,174 | A | 7/1910 | Fuchs | |
| 1,157,428 | A * | 10/1915 | Sheppard | 181/131 |
| 1,789,762 | A * | 1/1931 | Mackey | 181/131 |
| 1,845,795 | A * | 2/1932 | Joseph | 181/131 |
| 2,095,247 | A * | 10/1937 | Griffith | 181/137 |
| 2,566,687 | A | 9/1951 | Wehby | |
| 2,614,646 | A * | 10/1952 | Eaton | 181/157 |
| 2,651,380 | A * | 9/1953 | Brandenburg | 181/137 |
| 3,086,610 | A * | 4/1963 | Haas | 181/135 |
| 3,339,667 | A * | 9/1967 | Speelman | 181/137 |
| 3,504,760 | A | 4/1970 | Littman | |
| 3,547,219 | A | 12/1970 | Bothos | |
| 3,614,991 | A * | 10/1971 | Machlup | 181/137 |
| 3,735,836 | A * | 5/1973 | Littmann | 181/131 |
| 3,765,503 | A * | 10/1973 | Speidel | 181/137 |
| 4,299,303 | A | 11/1981 | Clark | |
| D269,295 | S * | 6/1983 | Bloom | D24/134 |
| 4,406,346 | A | 9/1983 | Pope, Jr. | |
| 4,569,413 | A | 2/1986 | Allen | |
| 4,768,612 | A * | 9/1988 | Hodson | 181/21 |
| 4,821,327 | A * | 4/1989 | Furugard et al. | 381/67 |
| 4,867,265 | A | 9/1989 | Wright | |
| 4,903,794 | A * | 2/1990 | Klippert et al. | 181/131 |
| 4,995,473 | A * | 2/1991 | Packard | 181/131 |
| 5,420,382 | A * | 5/1995 | Katz | 181/131 |
| 5,561,275 | A | 10/1996 | Savage et al. | |
| 5,663,532 | A | 9/1997 | Dieken et al. | |

(Continued)

*Primary Examiner*—Elvin G Enad
*Assistant Examiner*—Jeremy Luks
(74) *Attorney, Agent, or Firm*—David L. Nocilly; George R. McGuire; Bond Schoeneck & King, PLLC

(57) ABSTRACT

A stethoscope with a figure-eight configuration designed for one-handed operation and further comprising improvement to the headpiece resonance chamber. The ear tubes of the stethoscope are roughly S-shaped and together form a figure eight design. The lower portion of each ear tube is connected by a resistant force mechanism that maintains the stethoscope in the closed configuration. By applying one-handed compressive force to the resistant force mechanism attached to the lower portion of the stethoscope's figure-eight construction, the earpieces are separated and the stethoscope adopts the open configuration. Both the headpiece and the diaphragm are interchangeable to allow a variety of different shapes and sizes.

6 Claims, 3 Drawing Sheets

U.S. PATENT DOCUMENTS

| | | |
|---|---|---|
| 5,796,053 A | 8/1998 | Shieh |
| 5,847,330 A | 12/1998 | Grosslight |
| 5,917,918 A | 6/1999 | Callahan |
| 5,920,038 A | 7/1999 | Foster |
| 5,931,792 A | 8/1999 | Packard et al. |
| 6,244,376 B1 * | 6/2001 | Granzotto .................. 181/131 |
| 6,279,677 B1 * | 8/2001 | Sanchez-Zambrano ...... 181/131 |
| 6,308,798 B1 | 10/2001 | Rashman et al. |
| 6,499,560 B1 | 12/2002 | Lang et al. |
| 6,514,213 B1 | 2/2003 | Moteki |
| 6,691,821 B2 * | 2/2004 | Oster et al. ................ 181/131 |
| 6,883,639 B1 | 4/2005 | Lam et al. |
| 2003/0221903 A1 | 12/2003 | Roby et al. |
| 2007/0080017 A1 * | 4/2007 | Stickley ..................... 181/131 |

\* cited by examiner

STETHOSCOPE WITH ONE-HANDED OPERATION

BACKGROUND OF THE INVENTION

1. Field of the Invention

The present invention relates to stethoscopes, and, more particularly, to a stethoscope with one-handed operation.

2. Description of Prior Art

Stethoscopes are medical instruments used by medical professionals to detect sounds produced by the heart, lungs, abdomen, and other structures in both humans and animals. Sounds within the body cause the stethoscope's diaphragm to vibrate, resulting in acoustic waives that travel via air-filled tubes to earpieces placed into the user's ears. A traditional stethoscope is thus typically composed of a sound receiver assembly with a diaphragm and resonance chamber, flexible single or dual lumen tubing, two ear tubes, and two earpieces.

Physicians, nurses, and technicians use stethoscopes to monitor and diagnose illness, among other uses. However, these medical professionals are often performing other tasks when using the stethoscope, such as palpating the patient's pulse, holding the patient's chart, or manipulating equipment like a sphygmomanometer or thermometer. The design of a traditional stethoscope requires two hands to pull apart the ear tubes for placement of the earpieces into each ear. A one-handed stethoscope, however, would allow a physician or nurse to manipulate equipment or perform other functions while operating the stethoscope.

Veterinarians also use stethoscopes to detect internal sounds produced by pets, livestock, and other animals. Often, veterinarians must hold down or subdue an anxious and agitated animal while attempting to hear the animal's internal noises, or must displace an animal's leg or other body part to allow access to vital areas. Manually separating the two ear tubes of a traditional stethoscope to place the earpieces in each ear requires two hands. A one-handed stethoscope would allow a veterinarian to subdue, soothe, or manipulate an animal with one hand while separating the ear tubes with the other.

Traditional stethoscopes typically have a headpiece with one or two diaphragms and a shallow circular concave bell resonance chamber. In can be difficult to manipulate this large headpiece into narrow or hard-to-reach areas. For example, veterinarians often have difficulty placing a traditional headpiece behind the elbow of a dog, cat, or horse to hear internal sounds. It is also difficult to apply force to the headpiece while displacing the animal's elbow or other body part. A slim headpiece with a slanted design would easily slip into location behind the animal's body part and would allow the veterinarian to apply the necessary pressure.

Using standard headpieces often requires that the physician or veterinarian apply pressure directly to the headpiece and can cause the user's hands to touch the patient. As a result, vibrations to the diaphragm can be reduced, thereby interfering with auscultation of diagnostic sounds. A slanted or extended headpiece would allow the user to apply pressure to the headpiece without touching the patient or interfering with vibrations.

SUMMARY OF THE INVENTION

It is therefore a principal object and advantage of the present invention to provide a stethoscope with a configuration that allows one-handed placement in and removal from the user's ears.

It is a further object and advantage of the present invention to provide a slanted stethoscope headpiece with an elliptical cross-section and interchangeable diaphragms for improved manipulation and auscultation.

It is also an object and advantage of the present invention to provide tapered earpieces to facilitate separation of the stethoscope's ear tubes.

It is a further object and advantage of the present invention to provide protection and aesthetic design for the reverse side of a stethoscope headpiece.

Other objects and advantages of the present invention will in part be obvious, and in part appear hereinafter.

In accordance with the foregoing objects and advantages, the present invention provides a stethoscope adapted for one-handed operation and using an improved headpiece to facilitate auscultation and manipulation.

In its preferred form, the present invention provides a stethoscope with generally S-shaped ear tubes arranged in a figure-eight configuration which allows the user to open and close the stethoscope with one hand. The upper portion of each ear tube is fitted with an earpiece for placement in the user's ears, while the lower portions of the ear tubes are connected together by a spring or other resistant force element that holds the earpieces in close proximity. Squeezing the lower portion of the figure-eight design counteracts the resistant force of the spring or other mechanism and opens the stethoscope by pushing apart the earpieces. In a preferred embodiment, the stethoscope has earpieces that are tapered along their entire length to encourage and facilitate separation of the ear tubes during one-handed operation.

A further embodiment of the present invention provides a stethoscope headpiece with a circular base optionally containing a diaphragm, and an oblique cone having straight walls connected the circular base to the stethoscope tubing. The narrow end of the oblique cone connects to the tubing while the broad end of the cone connects to the circular base. In the preferred embodiment, the oblique cone is slightly flattened such that the cone is oval along its length, forming an elliptical oblique cone.

The diaphragm of the headpiece can be removable such that diaphragms of different sizes and shapes can be used depending upon the application. Additionally, as a result of the unique shape of the resonance chamber within the headpiece, it can be used to detect and monitor sound without any diaphragm. In this embodiment, the circular base of the headpiece has an opening that allows sound to directly enter the resonance chamber within the elliptical oblique cone.

In another embodiment of the present invention, the stethoscope headpiece is covered by an insulating foam covering that may be shaped in a variety of functional or aesthetically pleasing configurations.

BRIEF DESCRIPTION OF THE DRAWINGS

The present invention will be more fully understood and appreciated by reading the following Detailed Description in conjunction with the accompanying drawings, in which:

FIG. 5 is top perspective view of the improved headpiece design;

FIG. 6 is a cross-sectional view of the improved headpiece design taken along axis A-A of FIG. 5.

FIG. 7 is a detailed cross-section of a portion of FIG. 6;

FIG. 8 is a cross-sectional view of the improved headpiece design taken along axis B-B of FIG. 6.

FIG. 9 is a top view of the headpiece with a shaped foam headpiece covering.

DETAILED DESCRIPTION OF THE INVENTION

Figure 1:
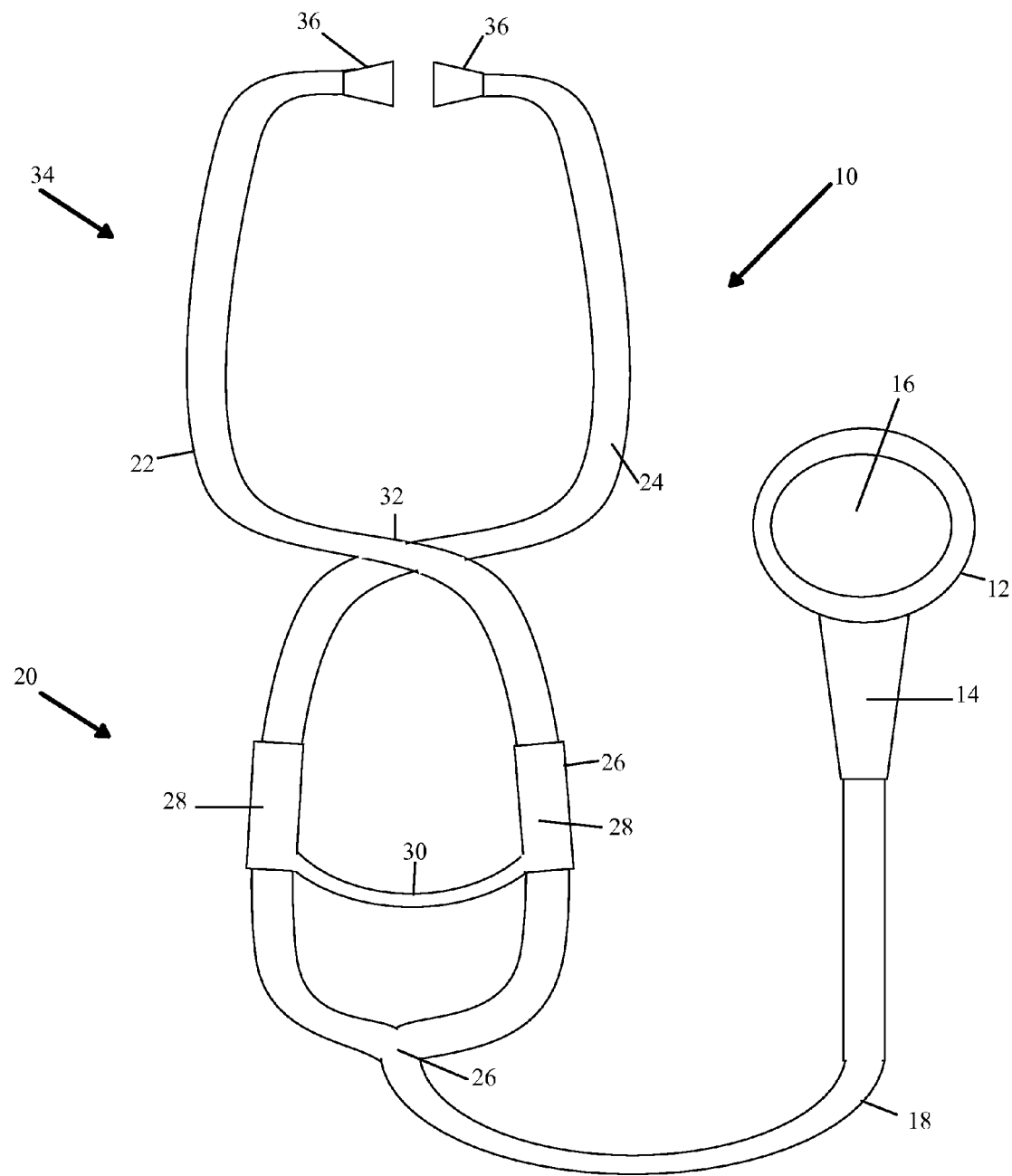
FIG. 1 is a front view of the present invention in the closed configuration.

Referring now to the drawings wherein like reference numerals designate identical or corresponding parts throughout the several views, there is shown in FIG. 1 a front view of the present invention in the closed configuration. The stethoscope 10 includes a conical headpiece 12, which has an oblique conical body 14 and a diaphragm 16. Headpiece 12 is attached to one end of tubing 18. Tubing 18 can be made from plastic, rubber, PVC, neoprene, or any other flexible substance and can have a single lumen or a dual lumen.

The other end of tubing 18 connects to the lower portion 20 of two ear tubes 22 and 24. In the preferred embodiment, tubing 18 branches into a U or Y configuration 26 to create two ends for connection to ear tubes 22 and 24, but other methods of connecting the tubing to the ear tubes will be known to those skilled in the art.

Ear tubes 22 and 24 are roughly S-shaped and can be made of plastic, metal, or other comparable material that provided at least some rigidity. Clamped or connected to lower portion 20 of ear tubes 22 and 24 is a resistant force element 26 having two attachment portions 28 held in relations by a spring 30, such as a resilient strip of metal. Spring 30 exerts a continuous extension force on lower portion 20 to keep the stethoscope in the closed configuration, such as when operatively worn by a user.

Upper portion 34 of ear tubes 22 and 24 forms an elongated semi-circle and gradually curves for proper placement of two opposing earpieces 36 in each ear of a user. Earpieces 36 can be of a traditional configuration known to those skilled in the art or can be tapered along their entire length, with the narrowest portion connected to the ear tubes and ending with a concave tip at the broadest portion, thereby minimizing interaction between the two earpieces during opening of the stethoscope.

Figure 2:
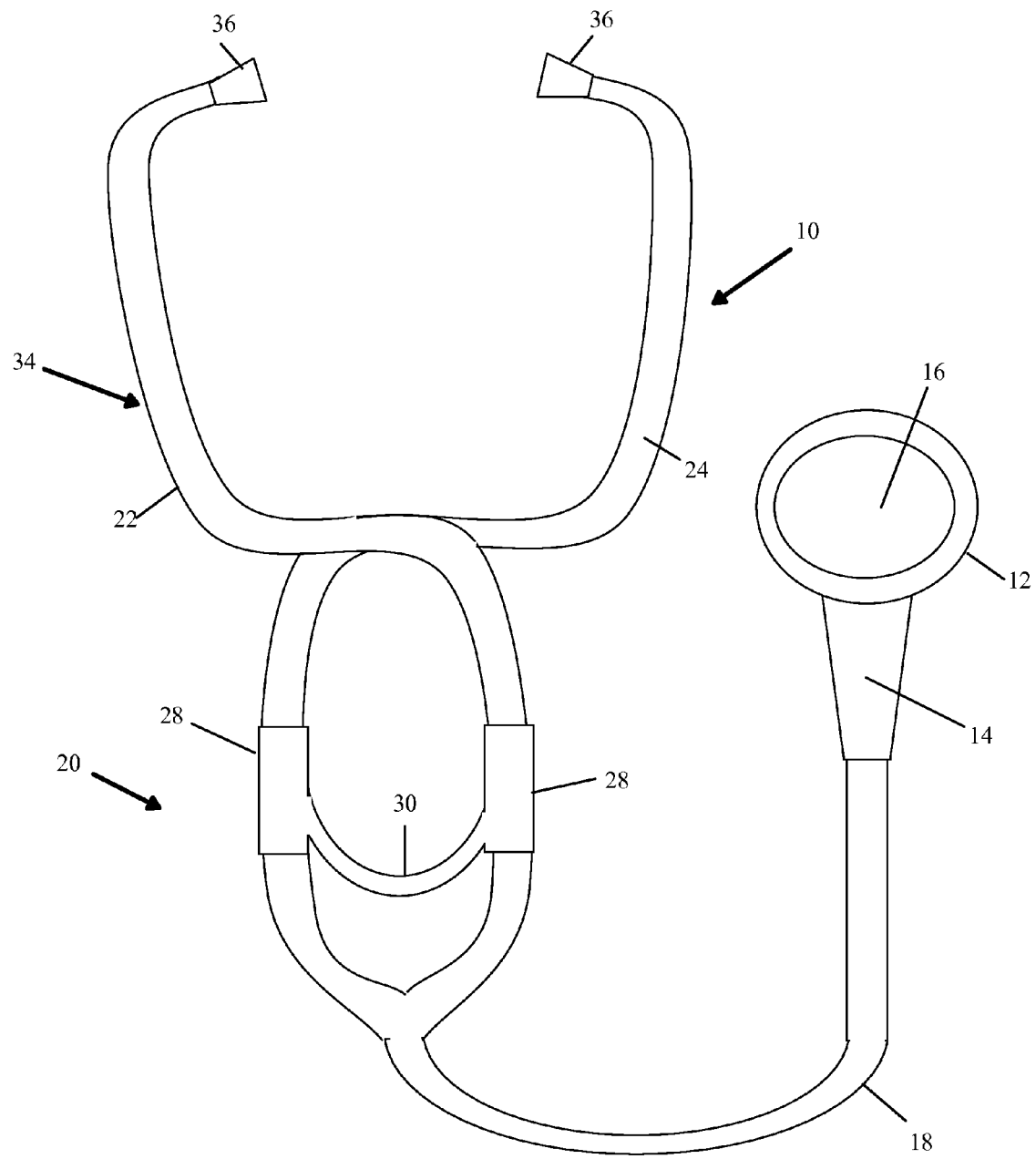
FIG. 2 is a front view of the present invention in the open configuration.

Referring to FIG. 2, separate ear tubes 22 and 24 of the present invention may be moved away from each other by compressing spring 30 of resistant force element 26 in one hand of user in the direction of the arrows. The compressive force causes earpieces 36 to separate with enough distance to allow placement in the ears of a user. By contrast, a user of a traditional stethoscope must grasp the ear tubes with both hands and pull them apart the other a sufficient distance for the earpieces to be inserted into the ears of the user.

Figure 3:
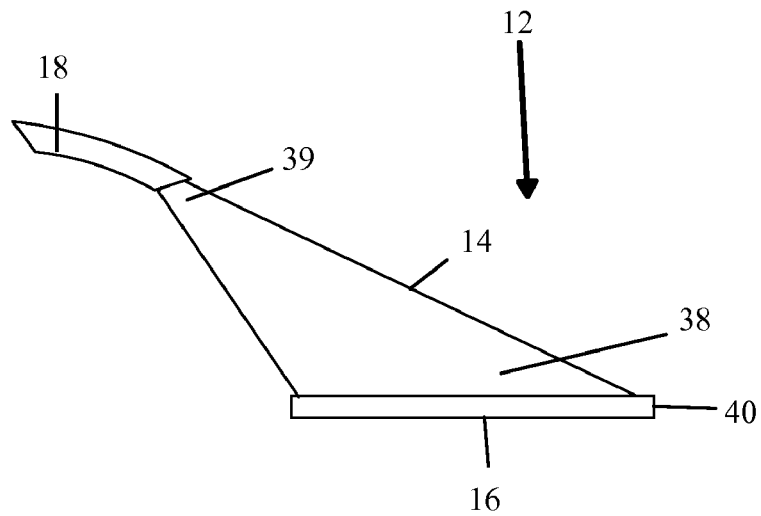
FIG. 3 is a side view of the improved headpiece design.

Referring to FIG. 3, there is seen an improved headpiece design according to the present invention. Headpiece 12 comprises an oblique cone 14 that extends from a substantially circular diaphragm 16 at a broad end 38 and to a narrow end 39 having a substantially circular opening in communication with the diaphragm for connection to tubing 18. Broad end 38 of headpiece 12 preferably terminates in a lip 40 that surrounds and holds diaphragm 16. Cone 14 of headpiece 12 is slanted to direct the sound waves along a direct path from diaphragm 16 to tubing 18. Additionally, force can be applied anywhere along the length of cone 14 by a user to push diaphragm 16 against a surface, such as the skin of a patient or animal.

Preferably, headpiece 12 is removably connected to tubing 18, and thus may be interchanged with other headpieces 12 to allow the use of a variety of different headpiece shapes and configurations with the present invention. Headpiece 12 can be manufactured from any material that will allow the capture and transmission of sound, including plastic or metal. In one embodiment, headpiece 12 is constructed from plastic such that the headpiece is lightweight and not cold to the touch.

Figure 4:
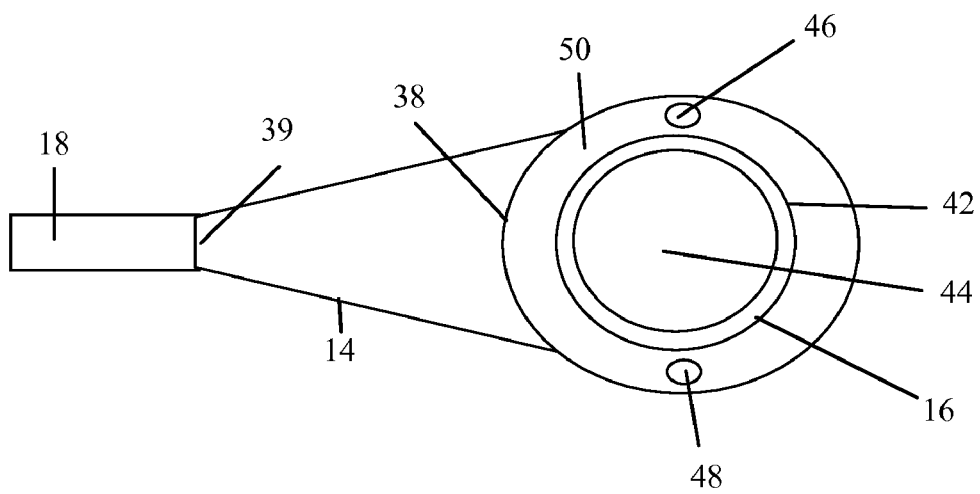
FIG. 4 is a bottom view of the improved headpiece design.

Referring to FIG. 4, diaphragm 16 may be surrounded by a ring 42 formed of hard rubber or plastic. Ring 42 is in turn surrounded by an elastic sheet 50 that covers the surface of lip 40. The elastic sheet may contain pegs that snugly fit into holes 46 and 48 optionally formed in lip 40 for removable attachment of diaphragm 16. Diaphragm 16 may also be configured to snap into a space formed into the broad end 38, or attached through other means known in the art. Diaphragm 16 can be interchanged with other diaphragms, thereby allowing for different sized diaphragms for different applications. In another embodiment, headpiece 12 includes a groove or lip on or near terminal portion 38 to allow for attachment of a variety of diaphragms 16 that connect by snap engaged with a groove or lip.

As seen in FIGS. 5-8, the oblique cone 14 of headpiece 12 preferably has an oval cross-section along cross-section B-B that results in a flattened headpiece 12, thereby allowing the device to be used in smaller or narrower spaces than conventional designs. As a result, headpiece 12 may be grasped more easily and farther from the patient or animal, thereby reducing vibrations and auditory interference. In addition, headpiece 12 affords better control over the pressure that is applied to headpiece 12 to hold it into contact with a patient or animal. Open end 39 is preferably positioned at ninety degrees to the axis of the cone of headpiece 12. In another embodiment of the present invention, headpiece 12 may comprise an imperfect ellipse formed by two circles offset at roughly thirty degrees from each other at the point where tubing 18 connects to cone 14. Headpieces 12 having the aforementioned designs will work even in the absence of a diaphragm. Thus, the present invention may omit the use of a diaphragm. In addition to the described embodiments of headpiece 12, however, the one-handed design may be used with any headpiece that allows the transmission of sound from the diaphragm to the tubing, albeit without the benefits provided by the improved headpiece 12 of the present invention.

Referring to FIG. 9, headpiece 12 may further include a shaped foam headpiece covering 50 comprises of a thin, insulating layer 52 that may be shaped in a variety of functional or aesthetically pleasing configurations. Layer 52 may be composed of plastic, rubber, foam, metal, or any other rigid or semi-rigid material. The structure of layer 52 may serve as insulation, surfaces for holding the headpiece in place or applying pressure, a means of holding interchangeable diaphragms in place, or to aid in the device's aesthetic appearance. Layer 52 can be removably attached to headpiece 12 or can be permanently attached to an interchangeable headpiece. As seen in FIG. 9, layer 52 may be formed into a dove or other icon, such as a cross, to improve the aesthetic nature of headpiece 12.

Although the present invention has been described in connection with a preferred embodiment, it should be understood that modifications, alterations, and additions can be made to the invention without departing from the scope of the invention as defined by the claims.

What is claimed is:

1. A headpiece for interconnection to a tube of a stethoscope, comprising:

a conical body extending uniformly along an oblique axis from a first circular opening of a first diameter to a second opening of a second diameter and having an elliptical cross-section perpendicular to said oblique axis;

wherein said second diameter is smaller than said first diameter and is dimensioned for interconnection to said tube of said stethoscope; and wherein said axis intersects said first opening at an acute angle.

2. The headpiece of claim 1, wherein said body includes an elliptical transverse cross-section extending along at least a portion of said axis.

3. The headpiece of claim 2, wherein said first opening is round.

4. The headpiece of claim 3, wherein said second opening is round.

5. The headpiece of claim 4, wherein said first opening includes means for attaching a diaphragm in covering relation thereto.

6. The headpiece of claim 5, wherein at least a portion of said headpiece is covered by a layer of insulation.

* * * * *